United States Patent [19]

Raveendranath et al.

[11] Patent Number: 5,210,081
[45] Date of Patent: May 11, 1993

[54] ALKALI METAL 8,9-DEHYDROESTRONE SULFATE ESTERS

[75] Inventors: Panolil C. Raveendranath, Plattsburgh, N.Y.; John A. Wichtowski, Albans, Vt.

[73] Assignee: American Home Products Corporation, New York, N.Y.

[21] Appl. No.: 841,694

[22] Filed: Feb. 26, 1992

[51] Int. Cl.$^5$ .................... A61K 31/56; C07J 53/00; C07J 31/00
[52] U.S. Cl. ................... 514/179; 552/503; 552/626
[58] Field of Search ............... 514/179; 552/503, 626

[56] References Cited

U.S. PATENT DOCUMENTS

| | | | |
|---|---|---|---|
| 2,834,712 | 5/1958 | Beall et al. | 167/74.5 |
| 3,079,410 | 2/1963 | Fritsch et al. | 552/503 |
| 3,394,153 | 7/1968 | Re | 260/397.45 |
| 3,608,077 | 9/1971 | Glasig | 424/243 |
| 3,649,621 | 3/1972 | Stein et al. | 260/239.55 |
| 4,061,744 | 12/1977 | Sugimoto et al. | 552/503 |
| 4,154,820 | 5/1979 | Simoons | 552/503 |

OTHER PUBLICATIONS

Black's Law Dictionary, 6th Ed, p. 286.

Primary Examiner—Marianne M. Cintins
Assistant Examiner—Kimberly J. Kestler
Attorney, Agent, or Firm—Richard K. Jackson

[57] ABSTRACT

This invention presents alkali metal salts of 8,9-dehydroestrone, its sulfate ester, and stable compositions thereof, as well as processes for their production. The sulfate ester salts are useful in estrogen replacement therapy.

10 Claims, No Drawings

ALKALI METAL 8,9-DEHYDROESTRONE SULFATE ESTERS

BACKGROUND OF THE INVENTION

The use of naturally occurring estrogenic compositions of substantial purity and low toxicity such as Premarin ® has become a preferred medical treatment for alleviating the symptoms of menopausal syndrome, osteoporosis/osteopenia in estrogen deficient women and as a preventative in the treatment of cardiovascular disease in men and women and in other hormone related disorders. The estrogenic components of the naturally occurring estrogenic compositions have been generally identified as sulfate esters of estrone, equilin, equilenin, $\beta$-estradiol, dihydroequilenin and $\beta$-dihydroequilenin (U.S. Pat. No. 2,834,712). The estrogenic compositions are usually buffered or stabilized with alkali metal salts or organic or inorganic acids at a substantially neutral pH of about 6.5 to 7.5. Urea has also been used as a stabilizer (U.S. Pat. No. 3,608,077). The incorporation of antioxidants to stabilize synthetic conjugated estrogens and the failure of pH control with Tris ® to prevent hydrolysis is discussed in U.S. Pat. No. 4,154,820.

8,9-Dehydroestrone is a known compound useful as an intermediate in the synthetic production of estrone by isomerization to 9,11 unsaturation (U.S. Pat. No. 3,394,153) and as an intermediate in the production of 3-cyclopentyloxy-17-ethynyl derivatives (Example XXVIII, U.S. Pat. No. 3,649,621).

DESCRIPTION OF THE INVENTION

In accordance with this invention there is provided alkali metal salts of 8,9-dehydroestrone and the alkali metal salts of 8,9-dehydroestrone sulfate ester free from other conjugated esters present in material found in natural sources of mixed esters. In addition, a stabilized alkali metal 8,9-dehydroestrone sulfate ester composition with tris(hydroxymethyl)aminomethane is provided. Furthermore, a process for the production of the alkali metal 8,9-dehydroestrone sulfate esters and their stabilized compositions is provided which affords excellent product control. The process of this invention differs from methods generally involved in the sulfation of steroids which are carried out by treatment of the steroid with aminesulfurtrioxide complexes followed by treatment with a cation exchange resin mediated by strong alkaline bases, preferably in hydroxylic solvents. Those reported methods for sulfation of steroids proved ineffective in the sulfation of 8,9-dehydroestrone. The process disclosed here relies upon the initial production of an alkali metal salt of 8,9-dehydroestrone followed by sulfation with trimethylaminesulfurtrioxide under mild conditions in a polar, aprotic solvent such as tetrahydrofuran with simultaneous or subsequent addition of tris (hydroxymethyl)aminomethane as a stabilizer. The alkaline bases employed in the production of the initial intermediates of 8,9-dehydroestrone are preferably sodium or potassium in the form of their hydrides and lithium as n-butyllithium.

The following examples illustrate the preparation of the alkali metal salts of 8,9-dehydroestrone by direct metallation with NaH, KH or n-butyl lithium in tetrahydrofuran under an inert atmosphere at about 0° C. The alkali metal salt containing solution is used directly in the sulfation reaction. The introduction if tris(hydroxymethyl)aminomethane at various stages of the process is also illustrated. Examples 6 and 7 illustrate the stabilizing influence of tris(hydroxymethyl)aminomethane.

EXAMPLE 1

Sodium 8,9-dehydroestrone-3-sulfate

To a stirred suspension of sodium hydride (0.24 g, 10 mmol) in tetrahydrofuran (20 mL), at 0° C., under nitrogen, was added a solution of 8,9-dehydroestrone (2.68 g, 10 mmol) in tetrahydrofuran (30 mL). After 10 minutes, the cooling bath was removed to allow the reaction mixture to attain room temperature. To this was added trimethylamine-sulfurtrioxide complex (1.39 g, 10 mmol). After stirring for 10 minutes, tris(hydroxymethyl)aminomethane (1.79 g, 15 mmol) was added and stirring continued overnight. The solvent was evaporated off and the residue taken up in water (180 mL) and washed with diethyl ether (2×50 mL). The aqueous solution was filtered using a sintered glass funnel (medium porosity) and the filtrate subjected to lyophilization to obtain 5.2 g of solid material.

Analysis Profile:

HPLC purity of sodium 8,9-dehydroestrone-3-sulfate—96.3%.

EXAMPLE 2

Sodium 8,9-dehydroestrone-3-sulfate

To a stirred suspension of sodium hydride (0.24 g, 10 mmol) in tetrahydrofuran (20 mL), at 0° C., under nitrogen, was added a solution of 8,9-dehydroestrone (2.68 g, 10 mmol) in tetrahydrofuran (30 mL). After stirring for 30 minutes at room temperature, tris(hydroxymethyl)aminomethane (1.79 g, 10 mmol) was added and after another 30 minutes trimethylamine-sulfurtrioxide complex (1.39 g, 10 mmol) was added and the solution was stirred overnight. The solvent was removed evaporatively and the residue was taken up in water (40 mL). The aqueous layer was washed with diethyl ether (2×20 mL) and then lyophilized to afford 5.1 g of solid material.

Analytical Profile:

HPLC purity of sodium 8,9-dehydroestrone-3-sulfate—96.2%.

EXAMPLE 3

Sodium 8.9-dehydroestrone-3-sulfate

To a stirred suspension of sodium hydride (0.24 g, 10 mmol) in tetrahydrofuran (20 mL), at 0° C., under nitrogen, was added a solution of 8,9-dehydroestrone (2.68 g, 10 mmol) in tetrahydrofuran (30 mL). After letting the reaction mixture warm to room temperature, it was stirred for 30 minutes and trimethylamine-sulfurtrioxide complex (1.39 g, 10 mmol) was added. Stirring continued overnight. Solvents were evaporated off and the residue taken up in water (50 mL), the aqueous layer was washed with diethyl ether (2×20 mL) and tris(hydroxmethyl)-aminomethane (1.21 g, 10 mmol) was added. The resulting clear solution was lyophilized to obtain 5.04 g of solid material.

Analytical Profile:

HPLC purity of sodium-8,9-dehydroestrone-3-sulfate—96.2%.

EXAMPLE 4

Lithium 8,9-dehydroestrone-3-sulfate

To a mixture of tris(hydroxmethyl)aminomethane (0.63 g, 5.2 mmol) and 8,9-dehydroestrone (0.94 g, 35 mmol) in the tetrahydrofuran (14 mL), at −70° C., under nitrogen, was added n-butyl lithium (2.5M solution in hexanes, 1.4 mL). After stirring at this temperature for 10 minutes, the cooling bath was removed. At 0° C., was added trimethylamine-sulfurtrioxide complex (0.49 g, 3.5 mmol), allowed to reach ambient temperature and continued stirring overnight. Solvents were evaporated off and the residue taken up in water (150 mL). This aqueous solution was washed with diethyl ether (3×35 mL) and lyophilized to afford 1.11 g of solid material.

Analytical Profile:

HPLC purity of lithium 8,9-dehydroestrone-3-sulfate—90.4 %.

EXAMPLE 5

Potassium 8,9-dehydroestrone-3-sulfate

To a stirred suspension of potassium hydride (0.14 g, 3.5 mmol) in tetrahydrofuran (14 mL) at 0° C., under nitrogen, was added tris(hydroxymethyl)aminomethane (0.63 g, 5.2 mmol), followed by a solution of 8,9-dehydroestrone (0.94 g, 3.5 mmol) in tetrahydrofuran (14 mL). After 15 minutes trimethylamine-sulfurtrioxide complex (0.48 g, 3.5 mmol) was added. After letting the reaction mixture reach room temperature, an additional quantity of tetrahydrofuran (15 mL) was added and stirring was continued overnight. Solvents were evaporated off and the residue was taken up in water (150 mL). This aqueous solution was washed with diethyl ether (3×35 mL) and subsequently lyophilized to obtain 1.63 g of solid material.

Analytical Profile:

HPLC purity of potassium 8,9-dehydroestrone-3-sulfate—91.3%.

From these procedures it can be seen that the process of this invention proceeds smoothly to provide highly pure product.

EXAMPLE 6

Sodium 8,9-dehydroestrone-3-sulfate

To a stirred suspension of NaH (0.57 g, 24 mmol) in tetrahydrofuran (50 mL) at 0° C., under nitrogen, was added a solution of 8,9-dehydroestrone (5.36 g, 20 mmol) in tetrahydrofuran (100 mL), over a period of 10 minutes. The reaction mixture was allowed to warm to room temperature and trimethylaminesulfurtrioxide complex (3.34 g, 24 mmol). Stirring continued for 24 hours. Solvent was removed and dry solids resuspended in diethyl ether and extracted with water (100 mL). The aqueous layer was separated, washed with diethyl ether (2×20 mL) and lyophilized to afford 5.65 g of solid material.

Analytical Profile:

HPLC strength of sodium 8,9-dehydroestrone-3-monosulfate—73.8%.

HPLC strength of sodium 8,9-dehydroestrone-3-monosulfate—33% (retested after two weeks).

EXAMPLE 7

Sodium 8,9-dehydroestrone-3-sulfate

To a stirred suspension of sodium hydride (0.72 g, 30 mmol) in tetrahydrofuran (50 mL) was added at 0° C., under nitrogen, tris(hydroxymethyl)aminomethane (5.38 g, 44 mmol) followed by a solution 8,9-dehydroestrone (8.04 g, 30 mmol) in tetrahydrofuran (110 mL). After allowing the reaction mixture to reach room temperature, trimethylamine-sulfurtrioxide (4.21 g, 30 mmol) was added and stirred for 24 hours. The reaction mixture was worked up as in Example 6 to afford 15.2 g of solid material.

Analytical Profile:

HPLC/GC strength of sodium-8,9-dehydroestrone-3-monosulfate—55.8%.

HPLC strength of sodium-8,9-dehydroestrone-3-monosulfate—55.3% (retested after two weeks).

HPLC strength of tris(hydroxylamine)aminomethane—30.9%.

Spectral Characterization:

$^1$H and $^{13}$CNMR (400 MHz)—consistent.

$^1$H NMR also indicates that the ratio of conjugated estrogen to tris(hydroxymethyl)aminomethane is about 1:1.5.

From Example 6, it is shown that in the absence of stabilization, the sulfate ester rapidly degrades while tris(hydroxymethyl)aminomethane provides protection from hydrolytic degradation as shown in Example 7 where the strength of the sulfate ester remained substantially constant over a two week period, thereby demonstrating better product control than obtained in the absence of tris(hydroxymethyl)aminomethane. The stabilized product is isolated in solid state, in a high state of purity and possesses desired water solubility properties at or near a neutral pH in conjunction with its pharmaceutical estrogenic activity.

The estrogenic activity of the compounds of this invention was established by administering them either orally or parenterally (subcutaneously) to rats and mice over a 7 day and 3 day period, respectively, and measuring the uterine weight gain in comparison with vehicle control. The results of these standard experimental procedures were as follows.

TABLE I

Estrogenicity of Sodium 8,9-Dehydroestrone-3-Sulfate - Rat Uterine Weight

| Treatment[a] | Dose[b] (µg) | Route | Wt. (mg) |
|---|---|---|---|
| Vehicle (oil) | — | s.c. | 46.3 ± 2.7 |
| Vehicle (dH$_2$O) | — | s.c. | 43.4 ± 3.5 |
| Sodium 8,9-dehydroestrone-3-sulfate | 0.1 | s.c. | 39.8 ± 2.1 |
| | 0.3 | s.c. | 46.1 ± 2.4 |
| | 1.0 | s.c. | 50.3 ± 2.7 |
| | 3.0 | s.c. | 71.9 ± 1.2 |
| | 10.0 | s.c. | 92.2 ± 5.7 |

[a]Six rats per group
[b]Daily dose over 7 days

TABLE II

Estrogenicity of Sodium 8,9-Dehydroestrone-3-Sulfate - Mouse Uterine Weight

| Treatment[a] | Dose[b] (µg) | Route | Wt. (mg) |
|---|---|---|---|
| Vehicle (dH$_2$O) | 0.3 ml | s.c. | 11.2 ± 0.3 |
| Sodium 8,9-dehydroestrone-3-sulfate | 0.1 | s.c. | 17.9 ± 3.0 |
| | 0.3 | s.c. | 18.9 ± 2.3 |
| | 1.0 | s.c. | 21.3 ± 2.6 |
| | 3.0 | s.c. | 23.1 ± 3.2 |
| | 10.0 | s.c. | 22.7 ± 0.8 |
| Sodium 8,9-dehydroestrone-3-sulfate | 0.3 | p.o. | 18.4 ± 1.4 |
| | 1.0 | p.o. | 14.6 ± 1.7 |
| | 3.0 | p.o. | 17.8 ± 0.4 |
| | 10.0 | p.o. | 19.1 ± 0.9 |
| | 30.0 | p.o. | 24.1 ± 1.1 |

[a]Four mice per group
[b]Total dose over 3 days

Thus, the alkali metal 8,9-dehydroestrone-3-sulfate esters of this invention are estrogens useful in replacement therapy in estrogen deficiency. Further, they are useful in suppression of lactation, prophylaxis and treatment of mumps orchitis, treatment of atherosclerosis and senile osteoporosis. For veterinary purposes, the steroids of this invention are useful in replacement therapy for underdeveloped females, incontinence, vaginitis of spayed bitches, in uterine inertia, pyometra and in retained fetal membranes.

When the steroids of this invention are employed as estrogenic agents in warm-blooded animals, they may be administered alone or in combination with pharmacologically acceptable carriers, the proportion of which is determined by the solubility and chemical nature of the compound, chosen route of administration and standard pharmacological practice. For example, they may be administered orally in the form of tablets or capsules containing such excipients as starch, milk, sugar, certain types of clay, and so forth. They may also be administered orally in the form of solutions which may contain coloring and flavoring agents or they may be injected parenterally. For parenteral administration, they may be used in the form of a sterile solution containing other solutes; for example, enough saline or glucose to make the solution isotonic.

This dosage of the present therapeutic agents will vary with the form of administration and the particular compound chosen. Furthermore, it will vary with the particular subject under treatment. Generally, treatment is indicated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is in the range of from about 0.02 mcgm. to about 500 mcgm. per kilo per day, although as aforementioned variations will occur.

What is claimed is:

1. A composition of matter consisting essentially of an alkali metal salt of 8,9-dehydroestrone-3-sulfate ester.

2. A composition of matter of claim 1 in which said alkali metal is sodium.

3. A composition of matter of claim 1 in which said alkali metal is potassium.

4. A composition of matter of claim 1 in which said alkali metal is lithium.

5. A composition of matter comprising an alkali metal salt of 8,9-dehydroestrone-3-sulfate in combination with tris(hydroxymethyl)aminomethane, said composition being free from other estrogenic steroids.

6. A composition of mater of claim 5 in which the ratio of tris(hydroxymethyl)aminomethane to alkali metal salt of 8,9-dehydroestrone-3-sulfate is from 1:0.5 to 0.5:1.

7. An alkali metal salt of 8,9-dehydroestrone-3-sulfate ester free from other estrogenic steroids.

8. A salt of claim 7 in which said alkali metal is sodium.

9. A salt of claim 7 in which said alkali metal is potassium.

10. A salt of claim 7 in which said alkali salt is lithium.

* * * * *